United States Patent [19]

Dee

[11] Patent Number: 4,844,070

[45] Date of Patent: Jul. 4, 1989

[54] CHANGEABLE SCALPEL BLADE AND CHUCK ASSEMBLY

[76] Inventor: Robert N. Dee, Box 512, Tuckahoe, N.Y. 10707

[21] Appl. No.: 104,450

[22] Filed: Oct. 2, 1987

[51] Int. Cl.$^4$ .............................................. A61B 17/32
[52] U.S. Cl. .................................... 128/305; 433/129; 433/144; 279/42; 30/338
[58] Field of Search ............... 128/303 R, 329 A, 305, 128/751, 752, 755, 318, 321, 320, 753, 754; 433/144, 129; 279/42; 604/22; 30/337, 338, 336

[56] References Cited

U.S. PATENT DOCUMENTS 2,465,433  3/1949  Doniger ................................ 30/336
4,513,754  4/1985  Lee ..................................... 128/754

Primary Examiner—Michael H. Thaler
Attorney, Agent, or Firm—Bauer & Schaffer

[57] ABSTRACT

A scalpel is provided including a chuck shaft having a diametric slot at its front end into which the rear end of a blade is inserted. The blade is provided with a cylindrical collar intermediate its ends which abuts against the front end of the chuck shaft. Over the blade and integral collar is threadedly mounted a retaining sleeve which engages with the exterior surface of the chuck shaft. As the retaining sleeve is threaded onto the chuck shaft, it radially compresses the front end of the chuck shaft so that the surfaces of the slot engage firmly and securely with the rear end of the blade, having previously been inserted therein.

5 Claims, 1 Drawing Sheet

CHANGEABLE SCALPEL BLADE AND CHUCK ASSEMBLY

BACKGROUND OF THE INVENTION

The present invention relates to a surgical instrument such as a dental scalpel and more specifically to an improved blade and chuck assembly for scalpels and similar knife-like instruments.

In my U.S. Patent Application No. 07/062113, filed June 13, 1987, U.S. Pat. No. 4,788,976, there is disclosed a dental scalpel having a universally adjustable blade in which the blade itself is removably connected and disconnected in a chuck. The necessity of providing a quick and easily detachable chuck and blade connection will be quite evident. On the other hand, the provision of a connection which secures against the introduction and accumulation of blood, virus and bacteria in through the instrument itself (i.e. chuck, handle or the like), while also evident, has only recently become essential due to the discovery of bacteria and viruses which resist normal sterilization procedures.

Various patents have been published relating to chuck and blade assemblies. For example, Ward U.S. Pat. No. 3,479,041 provides a blade interacting with a chuck assembly. Gleason U.S. Pat. No. 3,934,591 discloses a surgical knife interacting with a chuck assembly. Weinger U.S. Pat. No. 3,108,376 discloses a surgical blade having a rectangular mount removably engaging a correspondingly square-shaped opening member secured to a handle. Various dental accessory and blade attachments and/or assemblies are also disclosed in the following U.S. Pats. Nos: 4,525,144; 907,003; 1,316,685; 2,465,433; and 3,430,345.

Notwithstanding the variety of the known devices, none provides for quick and easy connection and disconnection while at the same time insuring against the egregious introduction of harmful bacteria and virus through the instrument itself. A further disadvantage found in the prior art devices is that each lacks full and complete structural support for the blade during its use and manipulation by the surgeon.

It is, therefore, a broad object of the present invention to provide a chuck and blade assembly for scalpels and the like which overcome the disadvantages of the prior art devices.

It is another object of the present invention to provide a secure fit for the blade which prevents lateral movement and/or spinning of the blade in the chuck.

A further object of the present invention is to provide barrier means which prevent the intrusion and/or accumulation of bacteria, virus and body fluids within the chuck or handle itself.

It is yet another object of the present invention to provide for maximum rigidity of the blade during use and to provide the shortest extending longitudinal distance of the blade from the chuck itself.

The foregoing objects as well as advantages, together with numerous other objects and advantages, are set forth in the following disclosure.

SUMMARY OF THE INVENTION

According to the present invention, a scalpel is provided including a chuck shaft having a diametric slot at its front end into which the rear end of a blade is insertable. The blade is provided with a cylindrical collar intermediate its ends which abuts against the front end of the chuck shaft. Over the blade and integral collar is threadedly mounted a retaining sleeve which engages with the exterior surface of the chuck shaft. As the retaining sleeve is threaded onto the chuck shaft, it radially compresses the front end of the chuck shaft so that the surfaces of the slot engage firmly and securely with the rear end of the blade, having previously been inserted therein.

In the preferred form, the blade and cylindrical collar are integrally formed, as in one piece, and the rear end of the blade is in the form of a flat tang conforming in shape to the slot within the chuck shaft. The inner surfaces of the retaining sleeve conform in diameter to the outer surfaces of the chuck shaft and the blade collar so that when the retaining sleeve is threaded into place, the surfaces make sliding engagement with each other. Preferably, since the material from which the blade and chuck members are formed is surgical steel, such engagement forms inherent sealing surfaces against the entry of fluids such as blood, including the bacteria and viruses carried thereby.

Full details of the present invention are set forth in the following description and are illustrated in the accompanying drawings.

DESCRIPTION OF THE INVENTION

Figure 1:
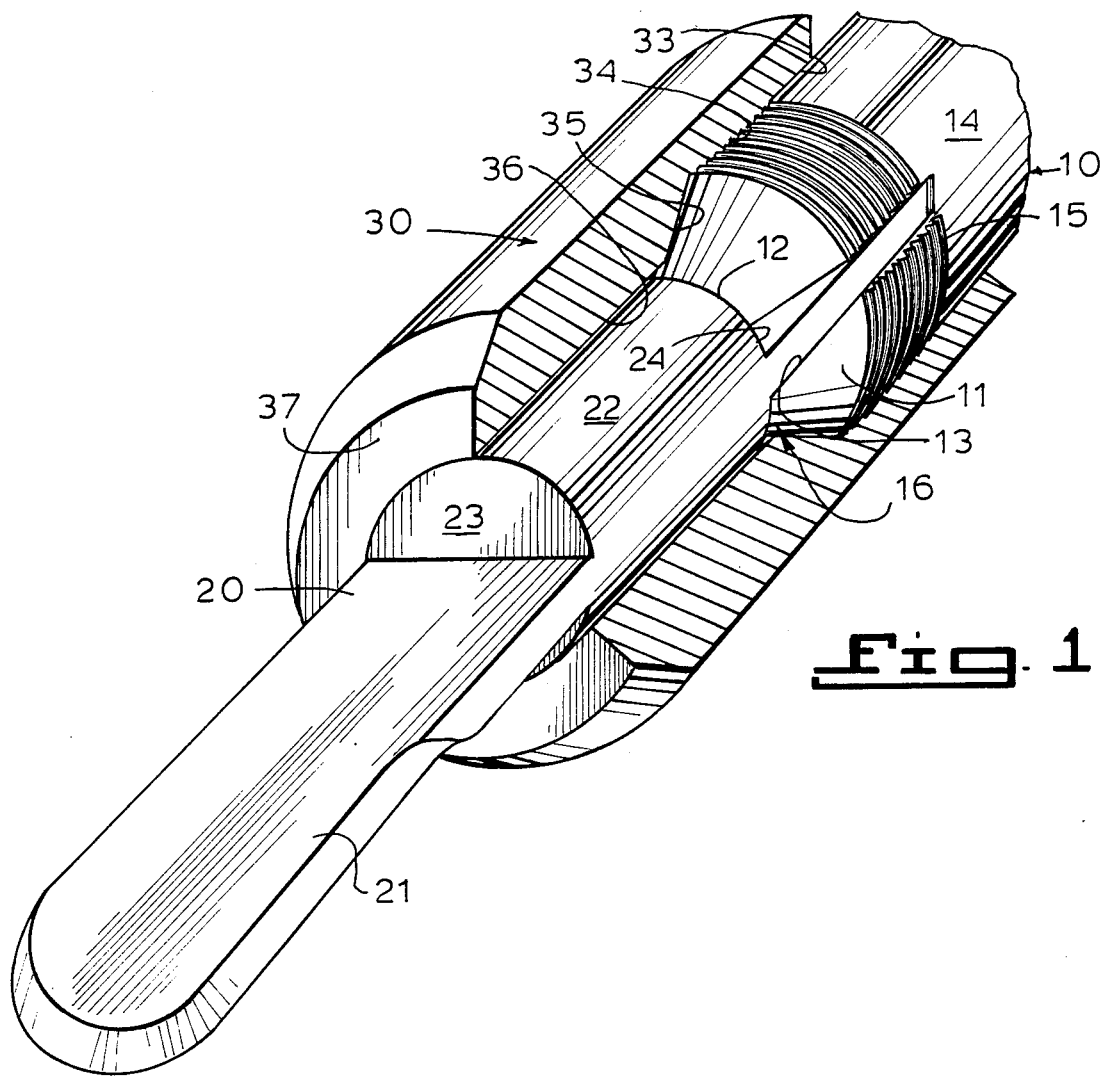
FIG. 1 is a perspective view, partially in section, showing the blade and chuck assembly embodying the present invention.

As seen in the figures, the blade and chuck assembly of the present invention comprises a chuck shaft 10, extending from a housing or handle (not shown) into which a blade 20 is secured by a retaining sleeve 30.

For the purpose of the simplicity of the description, the drawings do not illustrate the basic construction of the scalpel handle. The shaft 10 may be rigidly attached to the scalpel handle, or it may be, as shown in my aforementioned copending application, attached so as to be provided with a ball and socket joint so as to be universally journalled at the end of the scalpel handle or fixed stationarily at the end of the handle. Thus, the shaft may be rotatable or pivotable with respect to the not shown scalpel handle. Thus, it will be apparent to the reader that the present invention may be adapted to virtually any scalpel or similar knife-like cutting instrument.

In accordance with the present invention, the chuck shaft 10 is provided with a truncated conically tapered head 11 having a flat frontal face 12 into which is cut a diametric slot 13, the depth of which is selected to provide ample room for the rear or tang end of the blade 20 to fit thereon, as will be explained later. The outer surface 14 of the chuck shaft 10 directly behind the tapered head 11 is threaded as at 15 in a manner to receive the retaining sleeve 30.

The blade 20 is formed with a knife end 21 having a sharp edge about its entire, or part of its periphery. At the inner end of the knife edge, there is formed an integral collar 22 having a substantial axial length so as to assure a solid cylindrical shape. The collar 22 terminates in a frontal face 23, on the knife side and a rear face 24 on the trailing end. Extending from the rear face 26 coplanar with the knife 21 is a flat tang 25, or extension, which is adapted to fit snugly, i.e. frictionally, into the slot 13 on the chuck shaft 10.

The retaining sleeve generally depicted by the numeral 30 comprises a cylindrical body 31 having a smooth outer surface 31 and an inner surface having an enlarged diameter 33 at its rear end conforming to the chuck shaft 10 and being sequentially followed by a conical tapered intermediate section 35 conforming to the tapered head end 11 of the chuck shaft 10 and at the forward end with a small diameter portion 36 conforming to the outer diameter of the chuck collar 22. The forward or frontal end of the sleeve 30 is provided with a face 37 which closes the sleeve 30 and which forms with the frontal face 23 of the blade collar 22 a smooth, flat surface, perpendicular to the access of the blade.

Figure 2:
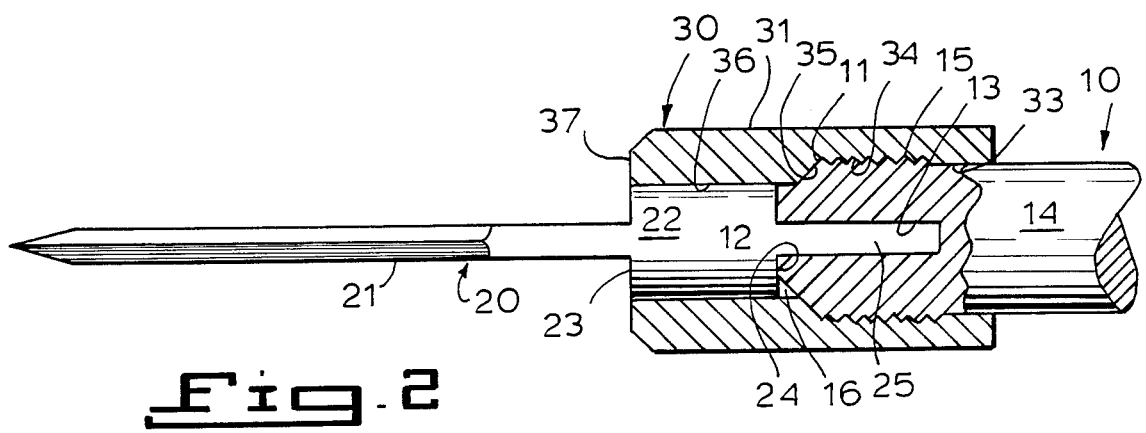
FIG. 2 is a side elevational view, partially in section, showing the blade and chuck assembly of FIG. 1.

The blade and chuck are assembled by inserting the tang 25 into the slot 13 of the chuck shaft so that, as will be seen in FIG. 2, the frontal face 12, at the head end of the shaft 10, abuts the rear face 24 of the blade collar 22. The conical head 11 of the shaft 10 has a taper such that a small annular space 16 is created within the retaining sleeve 30, at the head end of the chuck 10. The annular space 16 is triangular in cross-section.

Finally, the retaining sleeve 30 is threaded onto the end of the chuck shaft 10 so that its conically tapered surface 35 abuts against the similarly tapered head 11 of the shaft 10. By continuing the threading of the retaining sleeve onto the chuck shaft 10, the pressure created on the head 11 of the chuck shaft 10 is such as to radially compress the two sections of the head end 12 formed by the diametric slot 13, firmly against the tang 25 of the blade 20 so that the entire blade is firmly and fixedly seated within the chuck shaft. Further, because of the cooperation of the tapering surfaces formed at the end of the chuck shaft and the retaining sleeve 30, the rear face 24 of the blade collar 22 is seated firmly against the frontal face 12 of the chuck shaft. This prevents the blade from sliding or slipping with respect to the chuck shaft itself. Still further, because of the conforming diameters of the inner surface of the retaining sleeve 30 and the chuck shaft and blade, frictional sliding contact is obtained between these parts which prevent a further movement of the blade, once the retaining sleeve is seated firmly on the chuck shaft.

Preferably, the chuck shaft 10, blade 20 and retaining sleeve 30 are made of surgical steel and are precisely machined so that the parts not only fit frictionally but fit easily and snugly on their abutting surfaces. Thus, since all the parts engage and abut squarely, the surfaces act as inherent sealing means preventing the flow of fluids such as blood, and the impurities it carries through the separations between the parts.

It is also possible to make one or more of the parts of plastic or metals other than surgical steel. The sleeve 30 can be so made. Also, the cylindrical collar 22 may be made of a rigid plastic (such as "Teflon" or the like) suitably secured as with an epoxy adhesive rigidly and firmly to the blade.

Thus, the blade is securely and firmly held in position and may be manipulated as desired by the surgeon without fear of disengagement. On the other hand, merely unthreading the retaining sleeve 30 will enable the blade 20 to be easily removed from the chuck shaft and replaced. The cylindrical collar 22 not only impedes but prevents the flow of bacteria and body fluids from the cutting edges of the knife into the aperture formed within the retaining sleeve. Because of the integral combination of surface points and the flat design of the blade 20 and particularly the tang 25, a minimal longitudinal distance, for the longitudinal extension of the blade 20 out of the chuck, is obtained.

The present invention thus provides a chuck assembly in combination with a blade having a function and a structure not found in the prior art and for which the advantages enumerated herein are clearly obtained.

The present invention has been described with respect to the preferred embodiment thereof. The invention, however, should not be so limited, or restricted to the illustration, but its scope should be defined by the appended claims.

What is claimed is:

1. A blade and chuck assembly for a scalpel or similar surgical instrument having a handle to which is secured one end of a chuck shaft, said chuck shaft having at its other end a diametric slot adapted to receive the rear end of a blade and a threaded outer surface, a blade having a knife edge at its forward end and a tang at its rear end adapted to fit in said slot in said shaft and a cylindrical collar integrally formed with said blade intermediate the ends thereof, a retaining sleeve fitting axially over said blade and the outer surface of said chuck shaft, the inner surface of said sleeve having a rear portion threaded to engage the threaded surface of said shaft and a forward cylindrical portion slidably engaging said collar, said sleeve being securable on said shaft to radially compress said shaft in the area of the slot to hold said tang in fixed engagement within said slot and to hold said sleeve in slidable sealing engagement with said collar.

2. The instrument according to claim 1, wherein the inner surface of said retaining sleeve and the outer surface of said chuck shaft are provided with correspondingly formed conical tapers engageable on threading the retaining sleeve onto the chuck shaft to apply pressure on the chuck shaft adjacent the slot thereof so as to compress said chuck shaft into engagement with said blade.

3. The instrument according to claim 1, wherein said chuck shaft is truncated at its forward end, and the rear end surface of the blade collar is perpendicular to the axis of said blade and frictionally engaged with the forward end surface of said shaft perpendicular to the axis of said shaft.

4. The invention according to claim 1, wherein said tang is a flat planar member extending rearwardly from the blade collar coplanar with the knife edge thereof, said tang frictionally engageable within the slot within said chuck shaft in the absence of said sleeve.

5. The assembly according to claim 1, wherein said chuck shaft and blade collar are formed with parallel abutting stop faces.

* * * * *